(12) United States Patent
Nesterov et al.

(10) Patent No.: US 6,549,805 B1
(45) Date of Patent: Apr. 15, 2003

(54) TORSION DIAGNOSTIC SYSTEM UTILIZING NONINVASIVE BIOFEEDBACK SIGNALS BETWEEN THE OPERATOR, THE PATIENT AND THE CENTRAL PROCESSING AND TELEMETRY UNIT

(75) Inventors: Vladimir I. Nesterov, Omsk (RU); Anatoly E. Akimov, Moscow (RU); Oleg M. Elistratov, Irvine, CA (US)

(73) Assignee: ClinicTech Inc., Austin, TX (US)

( * ) Notice: Subject to any disclaimer, the term of this patent is extended or adjusted under 35 U.S.C. 154(b) by 0 days.

(21) Appl. No.: 09/971,396

(22) Filed: Oct. 5, 2001

(51) Int. Cl.⁷ .................................................. A61B 5/04
(52) U.S. Cl. ...................................... 600/545; 600/544
(58) Field of Search ................................. 600/545, 544

(56) References Cited

U.S. PATENT DOCUMENTS

| | | |
|---|---|---|
| 4,031,883 A | 6/1977 | Fehmi |
| 4,195,626 A | 4/1980 | Schweizer |
| 4,690,142 A | 9/1987 | Ross |
| 4,951,674 A | 8/1990 | Zanakis |
| 5,108,361 A | 4/1992 | Hein |
| 5,365,939 A | 11/1994 | Ochs |
| 5,392,788 A | 2/1995 | Hudspeth |
| 5,458,142 A | 10/1995 | Farmer |
| 5,746,205 A * | 5/1998 | Virsu et al. .................. 600/544 |
| 5,755,230 A * | 5/1998 | Schmidt et al. ............. 600/544 |
| 5,769,878 A | 6/1998 | Kamei |
| 5,983,129 A | 11/1999 | Cowan |
| 6,097,981 A | 8/2000 | Freer |
| 6,224,549 B1 * | 5/2001 | Drongelen ................... 600/300 |
| 6,236,884 B1 * | 5/2001 | Hunter et al. ................ 600/544 |
| 6,292,688 B1 * | 9/2001 | Patton ......................... 600/544 |

* cited by examiner

Primary Examiner—Max F. Hindenburg
Assistant Examiner—Navin Natnithithadha
(74) Attorney, Agent, or Firm—Boris Leschinsky

(57) ABSTRACT

A biofeedback diagnostic system includes a triggering sensor and a central processing and telemetry unit having a block for producing a series of various type stimuli to a patient and an operator of the system. Two biofeedback loops are formed: central unit-patient-triggering sensor, and central unit-patient-operator. The triggering sensor remotely acquires the patient's brainwaves feedback to the stimuli and sends a digital signal back to the central unit. To improve the patient's intuitive response, an optoelectronic element is placed of the patient's forehead and illuminated with a laser light at a frequency of the patient's brainwaves theta-rhythm. To isolate the torsion component of the laser light, a cavity resonator is employed with a volumetric chamber having a size being some multiple of the transmission frequency of about 1.45 GHz.

11 Claims, 2 Drawing Sheets

TORSION DIAGNOSTIC SYSTEM UTILIZING NONINVASIVE BIOFEEDBACK SIGNALS BETWEEN THE OPERATOR, THE PATIENT AND THE CENTRAL PROCESSING AND TELEMETRY UNIT

BACKGROUND OF THE INVENTION

The present invention relates generally to a biofeedback medical diagnostic system. More particularly, the system of the invention utilizes remote noninvasive biofeedback signal between the operator, the patient, and the CPT (central processing and telemetry) device to determine a pathological condition of the patient. The biofeedback signal is generated subconsciously and is based on device enhanced intuition.

A variety of medical diagnostic systems are known in the art to determine the patho-physiological status of the patient in general and to diagnose a variety of ailments and their state of progression. A simple example of such a system is a visual diagnostic device based on critical fusion frequency such as described in the U.S. Pat. No. 6,129,436 by Treskov or the Russian Patents No. 339,280 and 1,076,087. In a self-administered test, the patient can gradually increase the frequency of a blinking light until the point of fusion is reached and the patient is unable to distinguish between individual bursts of light. The frequency of that fusion is indicative of the state of the patient's nervous system and can be tracked over time to monitor its changes. An improvement is described in the Russian Patent No. 814,337 wherein the test is administered before and after a physical exercise. Such systems have generally limited ability to indicate the variety of patient's conditions due to the fact that only a part of the nervous system responsible for processing a visual stimulus is involved with the test. Such complex phenomenon as a change in working ability or the state of tiredness of a patient frequently results from other changes in the nervous system that would go undetected by such a device.

The situation of playing a dynamic game is used in various psycho-physiological evaluation devices to determine the state of a variety of body functions. Examples include such functions as attention, memory and vision (Russian Patent No. 825,001); sensing and motor reactions (Russian Patent No. 850,043); ability to choose (Russian Patent No. 929,060); the function of following a moving object (Russian Patent No. 827,029); ability to find the ways out of the difficult situation (Russian Patent No. 878,258) and even the predictive abilities (Russian Patent No. 839,488).

A more comprehensive biofeedback device is described by Schweizer in the U.S. Pat. No. 4,195,626 and includes application of a variety of audible, visual, electrical or tactile stimuli in a specially designed biofeedback chamber. Moreover, a microprocessor controlled rhythmical pattern of these stimuli is proposed and is adjusted based on the patient's own reactions.

Ross et al. in the U.S. Pat. No. 4,690,142 suggests electro-neurological stimulation of specifically described places on the skin of the patient. Production of such tactile stimulation of the skin is used to generate electrical characteristics of the organism responsive to a particular condition. The system of the invention is also used to train the organism to change its reaction to the stimuli by concentrating on increasing or inhibiting the tactile sensation.

An even more sophisticated system involves detecting the patient's electrical brainwaves via electroencephalogram or EEG as measured from a number of electrodes attached to the patient's scalp. Several examples of EEG based biofeedback devices are worth mentioning here among a large number of such systems described in the prior art.

A multiple channel biofeedback computer is described in the U.S. Pat. No. 4,031,883 by Fehmi et al. which contains a number of monopolar electrical contacts applied to the scalp and the body of the patient and a computer for collecting, filtering and amplifying the electrical signals therefrom. The overall feedback signal is then presented back to the patient to create awareness of the function being monitored of for other purposes.

Ross et al. in the U.S. Pat. No. 4,800,893 describes a kinesthetic physical movement display in which a number of electrodes feed their respective signals to an EEG apparatus equipped with a video display. Generation of kinesthetic physical movements allows the user to produce desired thought patterns.

A method for treating a patient using an EEG feedback is described by Ochs in the U.S. Pat. No. 5,365,939 and involves selecting a reference site for determining a brainwave frequency and entraining it in both directions until a predetermined stop point is reached. Flexibility assessment is then conducted with respect to the ability of the patient to change the brainwave frequency.

A method and device for interpreting concepts and conceptual thoughts from a brainwave date of a patient and for assisting in diagnosis of a brainwave dysfunction is described is proposed by Hudspeth in the U.S. Pat. No. 5,392,788. A system is described to include a transducer for transmitting a stimuli to the patient, EEG transducers for recording brainwave signals, and a computer to control signal presentation, EEG signal recording and analysis. A comparison is made between the recorded EEG signals and a model of conceptual perceptional and emotional thought or as an alternative to the known EEG signals from healthy individuals to diagnose a brain dysfunction.

A method for determining the intensity of focused attention is proposed by Cowan et al. in the U.S. Pat. No. 5,983,129 and includes obtaining a frontal lobe brainwave EEG signal and subtracting it from a separately obtained reference EEG signal to produce the attention indicator signal.

Finally, an electroencephalograph based biofeedback system is described by Freer in the U.S. Pat. No. 6,097,981 in which a computer animation is maintained by the computer and presented to the patient while EEG response signals are simultaneously being obtained and analyzed. Results of the analysis are then used to control the animation. A provision is made to send the EEG signals from the head of the patient or user to the machine by remote infrared transmitter.

All the above systems suffer from a number of common limitations, which stem from their dependence on the conscious state of mind of the patient. Another limitation is that the patient himself is used to interpret the biofeedback signal rather then an independent entity such as an operator. Finally, hardware is used to obtain the EEG signals and transmit it via a wire or infrared method to the main data collection and computing apparatus.

One further improvement in the accuracy of biofeedback analysis is described in the Russian Patent No. 759,092 in which various biofeedback signals are assigned a certain value of relative weight by a dedicated designation unit acting based on individual characteristics of each patient or a test subject. Varying these weight factors allows the apparatus to customize the results of analysis for each individual user.

The use of magnetic and electromagnetic fields is also known in the art to remotely and non-invasively assess certain conditions of a patient or to influence his state of fatigue and abilities to perform certain functions.

Farmer et al. has described a device for monitoring a magnetic field emanating from an organism in the U.S. Pat. No. 5,458,142. It includes a magnetic field sensor containing a ferromagnetic core surrounded by a multi-turn fine wire. The sensor is used to record the magnetic fields of an organism for diagnostic purposes as well as to control a magnetic field generator in order to produce a therapeutic magnetic field complimentary to that of an organism.

A bio-magnetic analytical system is described by Zanakis et al. in the U.S. Pat. No. 4,951,674 and includes a number of fiber-optic magnetic sensors to obtain information about the magnetic field from various tissues in the body including the brain.

A device for influencing an organism is proposed by Hein in the U.S. Pat. No. 5,108,361 and involves exposing the patient to a number of short pulsed signals supplied with increasing or decreasing frequency to stimulate the cerebral waves.

U.S. Pat. No. 5,769,878 by Kamei suggests a device for non-invasive enhancing the immuno-surveillance capacity of a person by supplying a pulsed light to his forehead (while shielding the eyes) in the frequency range between 0.5 to 13 Hz and preferably in the frequency of the alpha wave band as measured from the EEG signals.

Finally, our Russian Patent No. 2,142,826 describes a method and device for increasing non-invasively the accuracy and output of an operator of a bio-location device by using a low frequency unipolar magnetic field.

The need therefore exists for a non-invasive diagnostic system excluding the conscious influence of the patient and his own interpretation of the biofeedback signal.

SUMMARY OF THE INVENTION

Accordingly, it is an object of the present invention to overcome these and other drawbacks of the prior art by providing a novel non-invasive diagnostic system using a central processing and telemetry device and an operator to interpret the biofeedback signal from the patient.

It is another object of the present invention to provide a diagnostic system capable of processing the biofeedback from both the patient and the operator.

It is a further object of the present invention to provide a diagnostic system in which the biofeedback from the patient is collected non-invasively.

It is yet a further object of the present invention to provide a diagnostic system in which a device is provided to enhance the intuition of the patient to facilitate the formation of the biofeedback signal from to the patient to the apparatus.

The diagnostic system of the invention includes a central processing and telemetry (CPT) device capable of providing a predetermined series of stimuli to both the operator and the patient. Such stimuli can be chosen of various types depending on the purpose of evaluation. They can be of optical (such as a screen of a monitor, a series of light diodes, etc.), sound (via headsets or speakers), or magnetic nature. A triggering sensor facilitates the biofeedback formation and transmittal from the patient to the CPT device via an analog-to-digital converter. Another biofeedback loop is formed in parallel between the operator and the patient. It is therefore the operator who is actively participating in the evaluation and interprets its results. To further increase the ability of the patient to intuitively cause the triggering sensor to send the feedback signal, a device called "cadistor" provides an intuition enhancement. This devise subjects the patient to a series of small level energy bursts with the frequency preferably coinciding with the theta rhythm of the patient's brainwaves.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENT OF THE INVENTION

A detailed description of the present invention follows with reference to accompanying drawings in which like elements are indicated by like reference letters and numerals.

Figure 1:
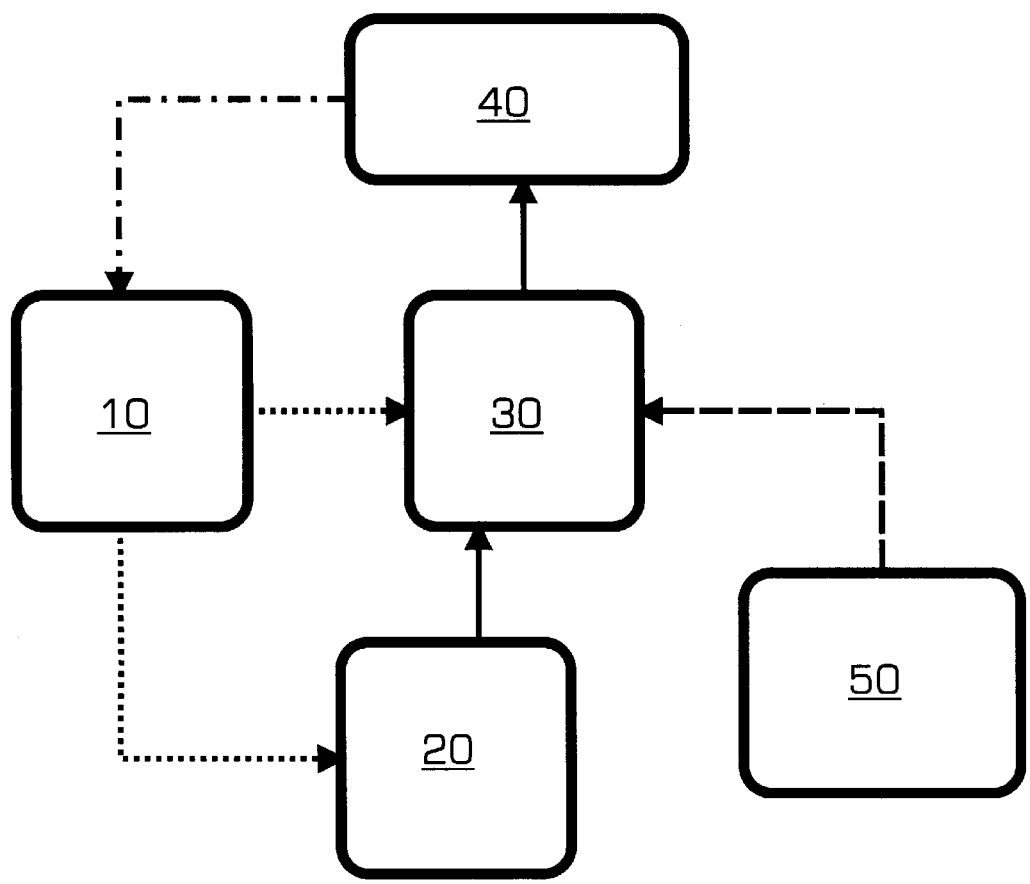
FIG. 1 is a general block-diagram of the diagnostic system of the present invention.

FIG. 1 shows the main block-diagram of the proposed system of the present invention. A CPT device 10 contains a situation-generating block designed to output a predetermined series of stimuli, also called "information codes" and transmits it through a dual peripheral device to both the operator 20 and the patient 30 (shown as dotted lines on FIG. 1). A number of appropriate peripheral devices can be employed with the system depending on the nature of the information code. Examples of such peripheral device include but not limited to: a magnetic induction coil for modulated magnetic field transmission, headsets or speakers for audio transmission, video monitor or a light display for visual signal transmission such as an image of the evaluated organ for example, etc. It is essential to point out that such information codes are transmitted to both the operator 20 and the patient 30, a unique feature of the diagnostic system of the invention.

A triggering sensor 40 collects the biological response from the patient 30 as an analog signal (solid line on FIG. 1), converts it into a digital one and sends it back to the CPT unit (dash-and-dot line on FIG. 1) as will be described in more detail below. The CPT unit is also equipped with the designation block for assigning specific relative weights to the input signals from the sensor 40 depending on individual characteristics of the patient.

Cadistor 50 is designed to work directly with the patient 30 to facilitate the work of the triggering sensor 40. It consists of a silicon-based semi-conductive transistor crystal acting as optoelectronic radioelement when illuminated by a light source such as a laser. Preferably, a silicon field-effect transistor is used in which a control area is in the form of a thin flat channel. When a laser light is directed at cadistor, an abrupt temporary short circuit is formed in the semiconductor and a small level of energy is released. Repeating of that process with high frequency caused periodic releases and accumulation of the energy. It has been established that the preferred wavelength of laser light is between 630 and 680 nanometers, the laser power should be below 5 MW and most importantly the light pulsation has to coincide with the theta-rhythm of the patient's brainwaves.

The cadistor is placed on the forehead of the patient about ½ of an inch above the nose and the eyes and symmetrical therebetween. Appropriate eye shielding and other precautions are recommended to avoid damage by the laser. The laser source is located only about 5–6 inches from the patient's forehead and is directed onto the cadistor placed on the patient's head as described above. Activation of periodic illumination of the cadistor with the laser light causes periodic release of the energy, which in this situation was clearly shown to increase the intuitive potential of the patient. It is also important to orient the cadistor properly in a space relative to one of the elements of the triggering sensor 40, namely its antenna.

In the above-described situation, both the electromagnetic and the torsion components of the laser light are directed at the patient. To block the electromagnetic component, a cavity resonator is deployed which prevents the electromagnetic component from getting through while forming and directing the torsion component as the only stimulus to effect the patient (dashed line on FIG. 1). The cavity resonator is typically made of metal and has a volumetric chamber with the size selected to be a multiple of the wavelength of the incoming signal, preferably about 1.45 GHz.

Figure 2:
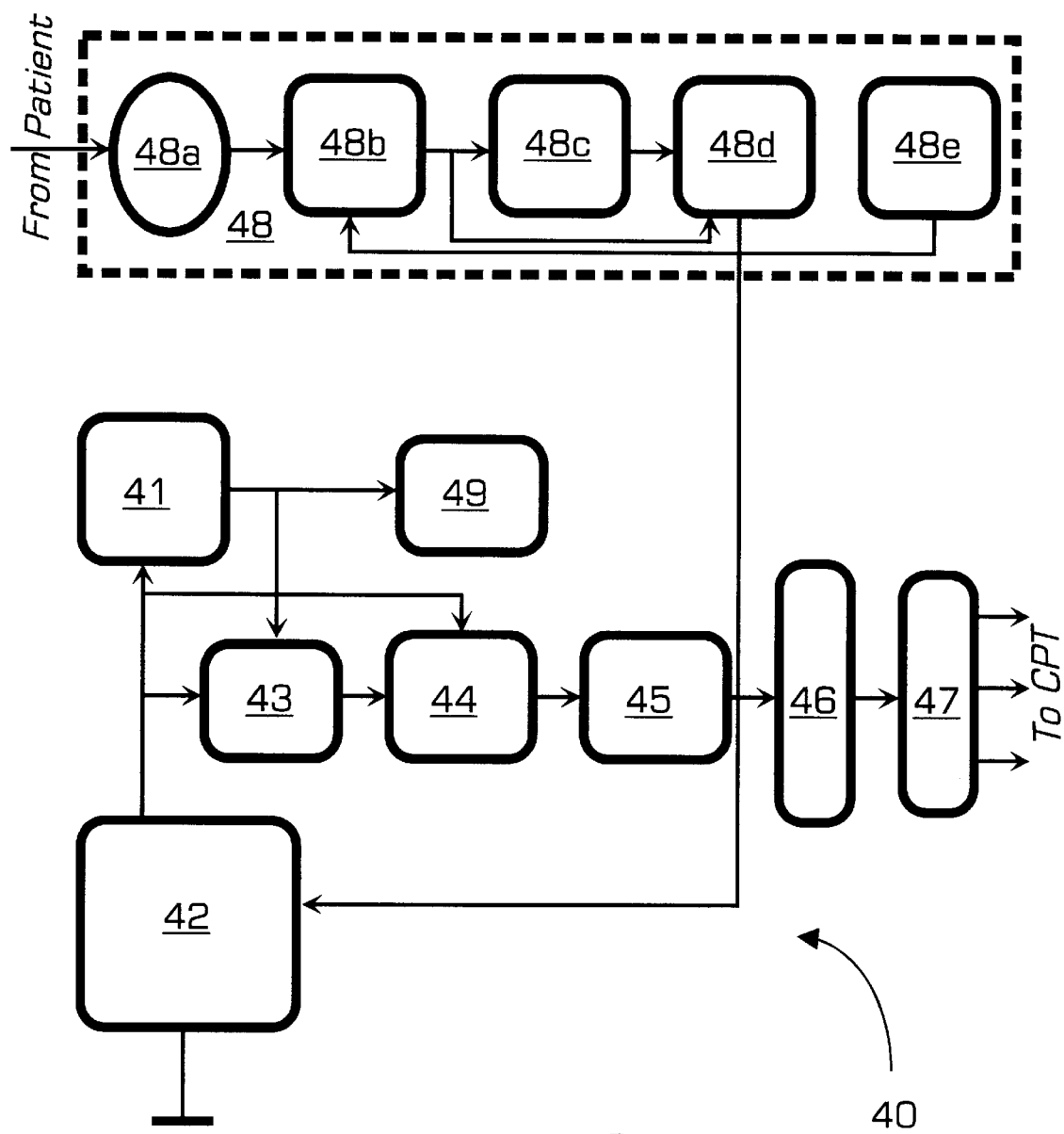
FIG. 2 is a general block-diagram of the triggering sensor of the diagnostic system.

FIG. 2 depicts the general block-diagram of the triggering sensor 40. It consists of a sensing element 41, integrator 42, source of electrical current 43, differential amplifier 44, amplifier 45, comparator 46, galvanic decoupling unit 47, and detector channel 48 designed to increase the influence of the patient on the sensing element 41. The detector channel 48 in turn consists of a logoperiodic antenna 48a, mixer 48b, rectifier 48c, discriminator 48d, and heterodyne 48e.

The function of the triggering sensor 40 is to sense the response produced by the patient in reaction to the information codes supplied by the CPT unit, transform them into a digital signal and send them back to the CPT unit 10. The sensing element 41 is the noise generator based for example on the radioelement 2G401V that is remotely subjected to the influence of the patient's brainwaves. A direct electrical current of an optimized value in the range of only several microamps, preferably between 1 and 5, is provided to power this element by power supply 49. This current is adjustable and is determined individually during the fine-tuning of the device in-vitro.

Electrical current source 43 consists of an operation amplifier such as for example the type UD25A (made by Voshod company in Kaluga, Russia) and an adjusting element such as a bi-polar transistor with low noise coefficient, for example the model KT3107L (made by Eleks company in Alexandrov, Russia) capable of supplying a consistent level of electrical current which is not effected by fluctuations of the power source voltage. The choice of low levels of such current is dictated by the desire to increase the sensitivity of the device to the outside disturbances.

The information signal is obtained from the sensing element 41 and taken through an amplifying phase consisting of a differential amplifier 44 and an amplifier 45. As a result, the signal is amplified with a total amplification factor of about 30 dB. The sensing element 41 is influenced by both the useful disturbances and random disturbances such as those from static electromagnetic fields. To eliminate such random disturbances, a precision differential amplifier 44 is used as a first phase of amplification. One possible type of such an amplifier may be INA 128UB by BUR BRAUN in which the signal voltage from the sensing element 41 is fed onto one input of the amplifier 44 while the other input is supplied with the same voltage after feeding it through the integrator 42. As a result, only the useful disturbance signal is allowed to go through to the next phase of amplification in the amplifier 45 while the noise signal is filtered out. Any appropriate commonly known amplifier can be used as an amplifier 45.

Comparator 46 can be of the type 521SA3 (made by NIIME company in Zelenograd, Russia) and is designed to transfer the analog signal from the amplifier 45 into a series of impulses such as for example in an A-D converter and then transmits it onto a galvanic decoupling unit 47 for further transformation.

The need for a galvanic decoupling unit 47 is dictated by the presence of random fluctuating electromagnetic noise fields from the power supply lines of the device itself as well as from other nearby located electrical devices. This device is designed to separate alternating component from direct current and contains an optical channel including a photo-diode PhD265A and an emitter AL107B made for example by Diode company in Moscow, Russia.

The detector channel 48 is designed to increase the influence of the patient to the sensing element 41. Reception is conducted in the short wave range, preferably at a frequency of 1.45 GHz , which is known to be in the range of radiowave transmission by human organs and tissues. Reception element is made with the help of logoperiodic antenna 48a which has a multi-turn spiral tapered design to ensure narrow direction of reception but in a wide range of transmission frequencies. The taper is oriented with the help of the laser pointer in such a way that its narrow portion is aimed directly at the middle of the front forehead of the patient about ½ inch above the eyes.

The mixer 48b is mounted preferably directly onto the antenna 48a and comprises a series of diodes (such as the type AA123 made by NIIPP company in Tomsk, Russia) onto which a voltage is fed from the heterodyne 48e. Such heterodyne is typically a sine voltage generator and is widely used in radio receivers. It is tunable simultaneously with the tuning of the oscillatory circuit of the receiver, to which the antenna is connected. This makes it possible to mark a stationary value of difference at a frequency between that of the received signal and the heterodyne signal in any position of the settings of a radio receiver. An example of an appropriate heterodyne is the one based on the diode of the type KA717B-4 produced by Nalchk's PP factory in Nalchik, Russia.

The rectifier 48c is designed to separate the low frequency phase from the useful signal, which is in turn fed into the discriminator 48d such as for example a differential amplifier INA128UB. Discriminator 48d subtracts the integrated signal from the raw signal and arrives at informational voltage bursts. Such voltage bursts are then fed back into the integrator 42 and further into the current source 43 which changes the value level of the current and shifts the power current of the sensing element 41. Such fluctuations of the current of the sensing element 41 ultimately effect the frequency spectrum of its operation and the frequency range of the useful signal produced thereby.

The diagnostic system of the present invention functions in the following way. Upon initiation of the test sequence, the CPT unit 10 generates information codes as electromagnetic, radio, audio, or light signals depending on the nature of evaluation. Such signals or stimuli influence the receptors of the nervous system of the operator 20 shifting it to a highly sensitive and reactive state and therefore increasing the strength of a biological feedback between the operator 20 and the patient 30. The action of the cadistor 50 assists the patient 30 in generating his influence as a useful disturbance signal for the sensing element 41 of the triggering sensor 40 thereby completing a second biofeedback loop between the CPT unit 10, the patient 30, and the triggering sensor 41.

EXAMPLE OF OPERATION

TABLE 1

| | Peripheral Device | | |
|---|---|---|---|
| | Magnetic Induction Coils | Video Monitor Stimuli | Stereo Headsets |
| Sequence | Electromagnetic Impulses Frequency of Coil Interruptions | Color Visual | Sound Audio (music notes) |
| 1 | 1.66 | Dark Maroon | DO |
| 2 | 2.49 | Red | RE |
| 3 | 3.32 | Orange | MI |
| 4 | 4.15 | Yellow | FA |
| 5 | 4.56 | Green | FA-Dies |
| 6 | 4.98 | Light Blue | SOL |
| 7 | 5.81 | Blue | LA |
| 8 | 6.64 | Violet | SI |
| 9 | 7.47 | Dark Violet | DO |

Table 1 presents one example of various stimuli to be generated by the CPT unit 10 of the diagnostic system of the present invention. The moments in time when each stimuli sequence begins are all coordinated with each other and with the initiation of the triggering sensor and cadistor so that the operator and the patient receive the stimuli and both loops of biofeedback are formed.

As a result, the CPT unit accumulates a response of the patient and the operator so that a database is formed of such responses for each series of individual stimulus. In case of electromagnetic impulses, only left part of the patient's brain is subjected thereto and only to the North portion of the magnetic impulse.

The studies conducted by the inventors have shown that the effect from the patient on the triggering sensor is more reproducible when the frequency of interruptions of electromagnetic impulses is close to that of the theta rhythm of the patient's brainwaves. That frequency tends to fluctuate towards increasing or decreasing depending on the state of health of the patient. In fact, a relationship is determined between the deviation in that frequency and the specific pathological conditions of certain body systems, selected organs, and even separate cells and chromosome fragments. Such relationship allows for specific diagnosis of a variety of pathological conditions. Examples include diagnosis of protrusions of spinal disks, remote metastases of various cancerous tumors, broken bones and trauma in general, blood vessel thrombosis, acute and chronic hepatitis, cirrhosis of liver, and a large variety of other pathological conditions. It is important to highlight that such diagnosis is possible to conduct using the subconscious level of brain function and therefore is independent of the patient's influence.

Another possibility of using the apparatus is to collect the digital signature of an organ as obtained by the triggering sensor with the library of available signatures collected previously from normal volunteers. Such comparison allows determining the degree of pathology and the state of disease development of the organ.

Further characterization of the disease state is possible using the following classification method developed by the inventors:

Class 0—ideal correlation of the digital signature of the organ under evaluation with the normal signature on file. Example—human egg cell at the beginning of the division process;

Class 1—the tissue of a healthy embryo before birth (without any body functions or toxins present);

Class 2—the tissue of a healthy newborn at the beginning of its life outside the mother, tissue functioning at the beginning stages;

Class 3—actively functioning tissue without toxins present;

Class 4—tissue with impaired function, toxin accumulation is just beginning;

Class 5—tissue with organic changes in which the toxins are accumulated within the cells of the tissue and actively restrict its function; and Class 6—extreme and irreversible state of organic damage and overall tissue disbalance.

Although the invention herein has been described with respect to a particular embodiment, it is understood that this embodiment is merely illustrative of the principles and applications of the present invention. It is therefore to be understood that numerous modifications may be made to the illustrative embodiment and that other arrangements may be devised without departing from the spirit and scope of the present invention as defined by the appended claims.

We claim:

1. A biofeedback diagnostic system comprising a central processing and telemetry unit and a non-invasive triggering sensor equipped with a noise generator, said central processing unit including a situation-generating block for producing a predetermined series of stimuli, said central processing unit also including a dual peripheral means for transmitting said stimuli in parallel to both an operator and a patient and therefore forming two biofeedback loops, consisting of both:

a) a first biofeedback loop including said central processing and telemetry unit sending said stimuli to said patient, said triggering sensor for remotely detecting said patient's brainwaves representing said patient's response to said stimuli, said triggering sensor further generating a signal in response to said brainwaves and sending it back to said central processing unit, and b) a second biofeedback loop including said central processing unit sending said stimuli to said operator, said operator affecting said patient to alter said patient's brainwaves, said triggering sensor reflecting said alteration in said signal back to said central processing and telemetry unit.

2. The biofeedback diagnostic system as in claim 1, wherein said stimuli is selected from a group consisting of magnetic, electromagnetic, audio, and visual stimuli.

3. The biofeedback diagnostic system as in claim 1, wherein said triggering sensor further including a detector channel equipped with a logoperiodic antenna to enhance detection of said patient's brainwaves.

4. The biofeedback diagnostic system as in claim 3, wherein said logoperiodic antenna is a multi-turn tapered spiral antenna for short wave reception at about 1.45 Ghz.

5. The biofeedback diagnostic system as in claim 1 further comprising an intuition enhancement means for assisting the patient in generating a response to said stimuli.

6. The biofeedback diagnostic system as in claim 5, wherein said intuition enhancement means including an optoelectronic radioelement and a light source directed thereon, said radioelement adapted for placement on a forehead of said patient.

7. The biofeedback diagnostic system as in claim 6, wherein said radioelement is a silicon-based field-effect transistor with a control area being a thin flat channel, said light source being a laser having the power of less than 5 MW, said laser controlled to illuminate said control area of said radioelement with pulses of light with the wavelength of between about 630 and 680 nanometers.

8. The biofeedback diagnostic system as in claim 7, wherein said pulses of light having a frequency coinciding with the patient's brainwaves theta-rhythm.

9. The biofeedback diagnostic system as in claim 8, wherein said intuition enhancement means further including a cavity resonator to block the electromagnetic component of said pulses of light while permitting the torsion components thereof to reach the patient.

10. The biofeedback diagnostic system as in claim 9, wherein said cavity resonator having a volumetric chamber with the size being a multiple of the wavelength of about 1.45 GHz.

11. The biofeedback system as in claim 1, wherein said central processing and telemetry unit further comprising a designation block for assigning specific relative weights to said signals from said triggering sensor.

* * * * *